US010633351B2

(12) United States Patent
Wang et al.

(10) Patent No.: US 10,633,351 B2
(45) Date of Patent: Apr. 28, 2020

(54) HALOGENATED COMPOUND AND AXIALLY CHIRAL ISOMER THEREOF

(71) Applicant: MEDSHINE DISCOVERY INC., Nanjing, Jiangsu (CN)

(72) Inventors: Jianfei Wang, Shanghai (CN); Yang Zhang, Shanghai (CN); Shuhui Chen, Shanghai (CN)

(73) Assignee: MEDSHINE DISCOVERY INC., Nanjing, Jiangsu (CN)

( * ) Notice: Subject to any disclaimer, the term of this patent is extended or adjusted under 35 U.S.C. 154(b) by 0 days.

(21) Appl. No.: 16/310,287

(22) PCT Filed: Jun. 13, 2017

(86) PCT No.: PCT/CN2017/088031
§ 371 (c)(1),
(2) Date: Dec. 14, 2018

(87) PCT Pub. No.: WO2017/215589
PCT Pub. Date: Dec. 21, 2017

(65) Prior Publication Data
US 2019/0337904 A1    Nov. 7, 2019

(30) Foreign Application Priority Data

Jun. 17, 2016  (CN) .......................... 2016 1 0440804
Jul. 4, 2016   (CN) .......................... 2016 1 0517979
Aug. 18, 2016  (CN) .......................... 2016 1 0693528

(51) Int. Cl.
*C07D 249/12*    (2006.01)

(52) U.S. Cl.
CPC ........ *C07D 249/12* (2013.01); *C07B 2200/07* (2013.01)

(58) Field of Classification Search
CPC .................................................. C07D 249/12
See application file for complete search history.

(56) References Cited

U.S. PATENT DOCUMENTS

| 8,084,483 B2 * | 12/2011 | Quart .................. C07D 249/12 514/384 |
| 2010/0267724 A2 | 10/2010 | Girardet et al. |
| 2016/0221970 A1 | 8/2016 | Quart et al. |
| 2018/0079731 A1 | 3/2018 | Wang et al. |

FOREIGN PATENT DOCUMENTS

| CN | 101083987 A | 12/2007 |
| CN | 101918377 A | 12/2010 |
| CN | 102186832 A | 9/2011 |
| CN | 103524440 A | 1/2014 |
| CN | 105399694 A | 3/2016 |
| CN | 105622531 A | 6/2016 |
| WO | 2010028190 A2 | 3/2010 |
| WO | 2015054960 A1 | 4/2015 |

OTHER PUBLICATIONS

Remington, The Science and Practice of Pharmacy, 21st Ed., Lippincott, Williams & Wilkins (2005), USA, Chapter 37, pp. 702-1057.
Berge et al., "Pharmaceutical Salts", Journal of Pharmaceutical Sciences 66: 1-19 (1977).
International Search Report of PCT/CN2017/088031 dated Jul. 27, 2017.
Written Opinion of PCT/CN2017/088031 dated Jul. 27, 2017.
English translation of priority application CN 201610440804.2, 2016.
English translation of priority application CN 201610517979.9, 2016.
English translation of priority application CN 201610693528.0, 2016.

* cited by examiner

*Primary Examiner* — Laura L Stockton
(74) *Attorney, Agent, or Firm* — Harness, Dickey & Pierce, P.L.C.

(57) ABSTRACT

A halogenated compound, an axially chiral isomer thereof, and an application thereof in preparing drugs for disorders closely related to aberrant levels of uric acid.

20 Claims, No Drawings

HALOGENATED COMPOUND AND AXIALLY CHIRAL ISOMER THEREOF

This application is a U.S. National Phase Application under 35 U.S.C. 371 of International Application No. PCT/CN/2017/088031 filed on Jun. 13 2017. This application claims priority to Chinese Application No. 201610440804.2, filed on Jun. 17, 2016, Chinese Application No. 201610517979.9, filed on Jul. 4, 2016, and Chinese Application No. 201610693528.0, filed on Aug. 18, 2016.

FIELD OF INVENTION

The present invention relates to a halogenated compound, an axially chiral isomer thereof, and an application thereof in preparing drugs for disorders closely related to aberrant levels of uric acid.

BACKGROUND OF INVENTION

Uric acid is a metabolite of purines in animals and human. For human, uric acid is excreted as the end-product of purine metabolism through the intestine and kidney in human body due to the lack of uricases which continue to oxidatively degrade uric acid to more water-soluble allantoin, and renal excretion is the main pathway for uric acid excretion in human body. The upper limit of normal uric acid concentration range in the human body is 400 umol/L (6.8 mg/dL) for male and 360 umol/L (6 mg/dL) for female. Aberrant levels of uric acid in the human body are often due to the increased production of uric acid or decreased excretion of uric acid, which usually include three types: increased uric acid production type, reduced uric acid excretion type and mixed type. Disorders closely related to aberrant levels of uric acid include hyperuricemia, gouty arthritis (also referred to as gout), kidney stones, urinary calculi, hypertension, etc.

Hyperuricemia refers to a disease in which the metabolism of purine substances in the human body is disordered, resulting in an increased uric acid production or a decrease in excretion, and an aberrantly high level of uric acid in the blood. When the concentration of uric acid is more than 7 mg/dL in human blood, uric acid is deposited as a monosodium salt in the joints, cartilage and kidneys, resulting in overreaction (sensitivity) of the body's immune system and causing pain, this symptom is called gouty arthritis. The general attack sites of acute gout are peripheral joints such as the big toe joint, ankle joint, knee joint and so on, and red, swollen, hot, and severe pain appear in the attack site of acute gout, which usually occurs in midnight and can make people wake up from sleep. Hyperuricemia is the pathological basis of gouty arthritis, and the use of drugs to decrease blood uric acid concentration is one of the common methods for preventing gouty arthritis.

In recent years, the attack of hyperuricemia and gout disease is on the rise as the change of lifestyle. In Europe and USA, researches on the epidemiology have shown that the incidence of gouty arthritis accounts for 1-2% of the total population and is the main type of arthritis in adult males. Bloomberg News estimates that there will be 17.7 million gout patients in 2021. In China, the survey shows that 25.3% of the population has a high blood uric acid concentration and 0.36% has gout diseases among the population aged 20 to 74. At present, clinical treatment drugs mainly include 1) inhibition of uric acid-producing drugs, such as xanthine oxidase inhibitors allopurinol and febuxostat; 2) uric acid excretion drugs, such as probenecid and benzbromarone; 3) inflammation inhibitors, such as colchicine and so on. These drugs have certain defects in treatment, including poor efficacy, large side effects, and high cost are some main bottlenecks in clinical application. It has been reported that blood uric acid levels of 40%-70% of patients who have received standard treatment did not meet the expected therapeutic goals (<6 mg/dL).

URAT1 is an important renal anion transporter located on the brush border membrane of the epithelial cells of the renal tubules, specifically transporting uric acid from the renal tubules to epithelial cells, which is the main driving force for uric acid reabsorption in the renal tubules. Therefore, if the urate transporter URAT1 can be significantly inhibited, it will increase the excretion of uric acid in the body, thereby lowering blood uric acid level and reducing the possibility of gout attack.

le;2qThe first URAT1 target inhibitor Leinurad of AstraZeneca showed in the figure below was approved by the FDA in December 2015. The 200 mg/day dose was approved in combination with xanthine oxidase inhibitor XOI (such as Febuxostat, etc.) for the treatment of hyperuricemia and gouty arthritis, but the additive effect of combination was not very significant compared with the xanthine oxidase inhibitor alone. The 400 mg/day dose of Leinurad was not approved due to significant toxic side effects at high doses (the incidence of kidney-related adverse events, especially the incidence of kidney stones), although the higher additive effect of combination appeared. Therefore, the FDA required the Leinurad label to be filled with a black box warning to warn the medical staff acute kidney failure caused by Leinurad, especially when not used in combination with XOI, and if the over-approved dose of Leinurad was used, the risk of renal failure is even higher. Meanwhile, the FDA asked AstraZeneca to continue its evaluation on kidney and cardiovascular safety after Leinurad marketed. For long-term drug use for a metabolic disease, the safety of the drug is particularly important. Therefore, there is a strong demand to develop a safe drug for lowing blood uric acid.

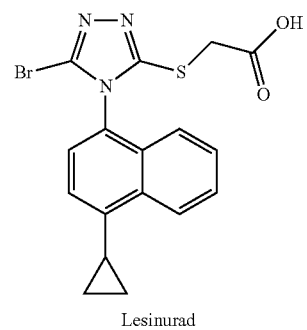 [SMILES: O=C(O)CSc1nnc(Br)n1-c1ccc(C2CC2)c2ccccc12]

Lesinurad

In the new drug declaration report disclosed by AstraZeneca, the results of the identification experiments of compound Lesinurad in liver microsomes and hepatocyte metabolites of various animal species in vitro were reported in detail. The data showed that M3 and M4, two major metabolites of Lesinurad was significantly detected in the monkey and human hepatocytes, but M3 and M4 were not detected in dog and rat hepatocytes, as shown in Table-1 below.

TABLE 1

| System | Species | M3 | M4 | Lesinurad | Total |
|---|---|---|---|---|---|
| liver microsome | rat | — | — | 100 | 100 |
|  | dog | — | — | 100 | 100 |
|  | monkey | 7.9 | — | 92.1 | 100 |
|  | human | — | — | 100 | 100 |
| hepatocyte | rat | — | — | 100 | 100 |
|  | dog | — | — | 100 | 100 |

TABLE 1-continued

| System | Species | M3 | M4 | Lesinurad | Total |
|---|---|---|---|---|---|
|  | monkey | 1.45 | 0.47 | 98.1 | 100 |
|  | human | 2.24 | 5.69 | 92.1 | 100 |

Meanwhile, AstraZeneca also reported the main metabolites and metabolic pathways of Lesinurad after administration in various genus animals, in which the bishydroxy metabolite M4 was specifically detected in human metabolites:

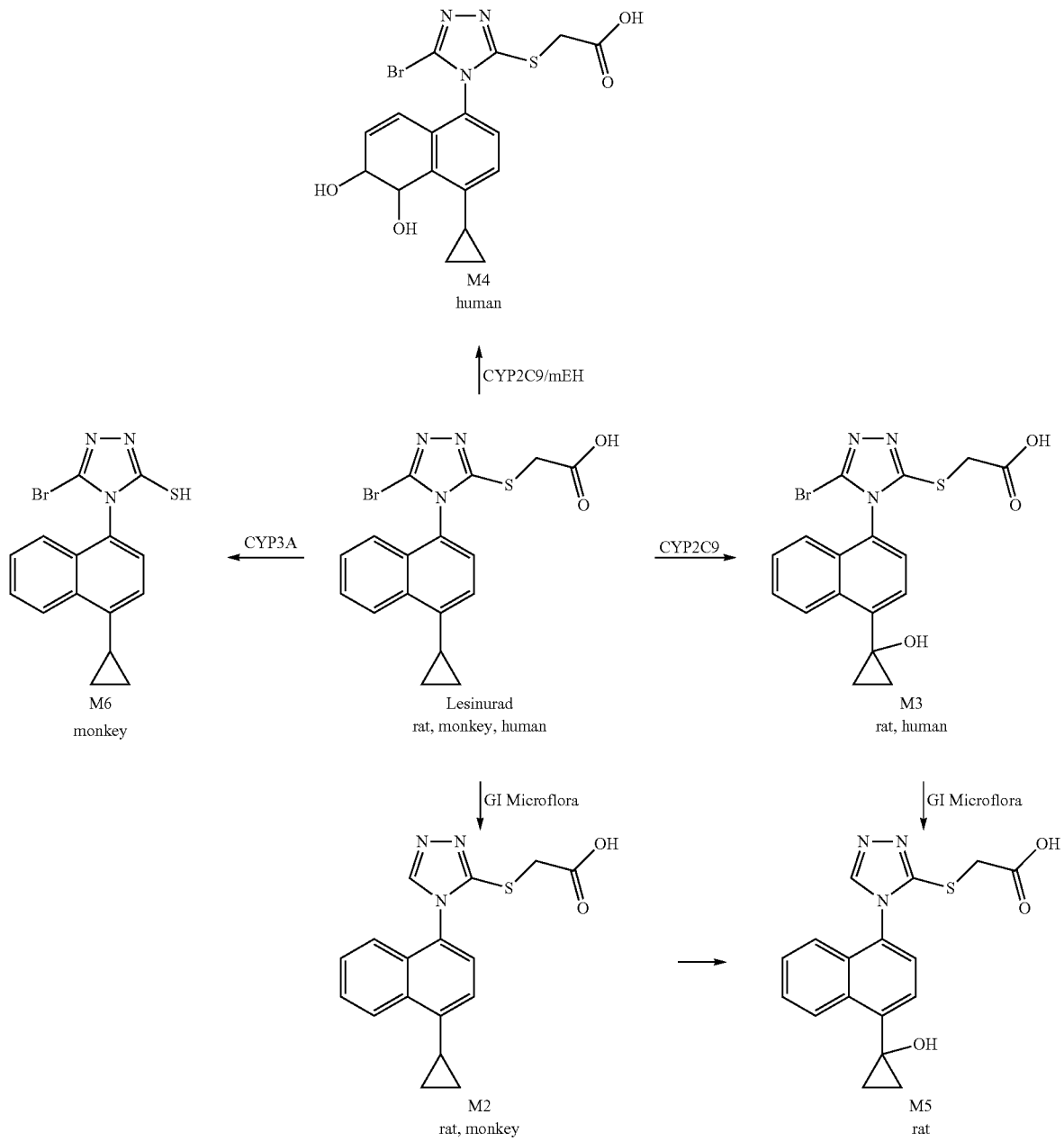

This was consistent with Lesinurad's clinical data. Experimental data showed that M3, M4 were the main metabolites found in human clinical, as shown in Table-2 below.

TABLE 2

| System | Time (h) | M1 | M2 | M3 | M3b | M4 | M5 | M5b | M16 | Other | Lesinurad | Total |
|---|---|---|---|---|---|---|---|---|---|---|---|---|
| | | | | | | Percentage of administered dose | | | | | | |
| Urine | 0-144 | 1.5 | 0.3 | 12.0 | 1.0 | 15.7 | ND | ND | 0.5 | 1.2 | 31.3 | 63.4 |
| Feces | 0-144 | ND | 4.8 | 0.3 | 1.9 | 5.0 | 3.6 | 7.8 | 1.1 | 7.5 | 1.5 | 33.5 |

The production pathway of M4 metabolite could be determined as a result of the co-action of cytochrome CYP2C9 and primate epoxide hydrolase mEH. This mEH metabolic pathway was unique to primate species, which explained why no M4 was observed in rats and dogs:

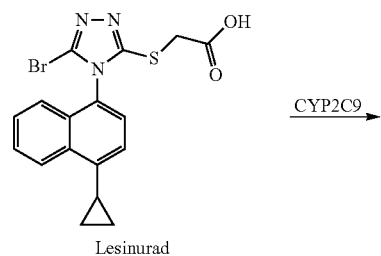
Lesinurad

↓ CYP2C9

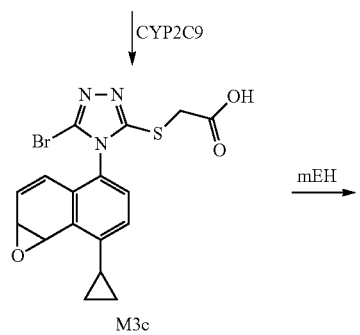
M3c

| mEH

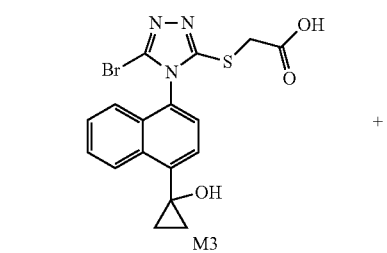
M3

+

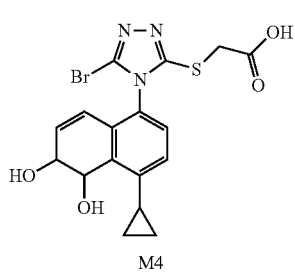
M4

-continued

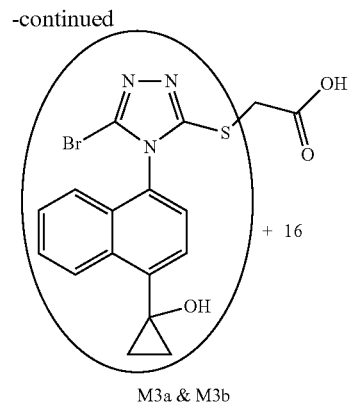
M3a & M3b

CONTENTS OF INVENTION

In view of the special metabolic pathway from Lesinurad to M3c and then to M4, the metabolites M3, M4 and its intermediate M3c (M3c is unstable and cannot be detected in vivo) may be one of the reasons for clinical toxic side effects. If the amount of the compound metabolites M3 and M4, particularly the amount of the epoxy intermediate M3c, can be effectively reduced, it is theoretically possible to reduce the clinical toxic side effects found in the compound Lesinurad in humans. These oxidation reactions are all derived from the ring system oxidation of electron-rich naphthalene rings. Therefore, if the electron cloud density of the naphthalene ring can be effectively reduced, the oxidation reaction should be slowed down or hindered, thereby reducing the generation of metabolites M3, M4 and its intermediate M3c.

Based on the study of the Lesinurad metabolic pathway and its clinical toxic side effects, a series of compounds containing a naphthalene ring substituent (formula I) were designed and synthesized in the present invention, in which two representative compounds (formulas II and V) were successfully separated to give the rotational isomers (formula III and formula IV, formula VI and formula VII). The inventors examined the ability of these compounds to inhibit the transport of labeled uric acid by MDCK cell lines stably transfected with the human URAT1 gene. We found that the substituent groups on the naphthalene ring were acceptable for cytostatic activity, and the inhibitory activity $IC_{50}$ in vitro was generally improved compared with Lesinurad; these compounds also showed better properties in rat pharmacokinetic experiments with the feasibility of being developed as a drug; more importantly, these compounds have been shown to produce fewer similar metabolites than the reference compound Lesinurad in metabolite identification experiments in vitro, which explained from the perspective of toxicity mechanism that when administrated in vivo, compared with Lesinurad, these substituted naphthalene ring compounds in the present invention may have less toxicity while maintaining activity and efficacy.

The present invention provides a compound represented by formula (I) or a pharmaceutically acceptable salt thereof,

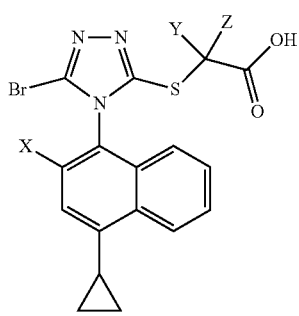
(I)

Wherein,

X is selected from F, Cl, Br and I;

each of Y and Z is independently selected from H, methyl, ethyl, cyclopropyl, cyclobutyl, cyclopentyl, cyclohexyl;

or Y and Z are linked together to form 3- to 6-membered ring.

In certain embodiments of the present invention, the compound is selected from a compound represented by formula (II).

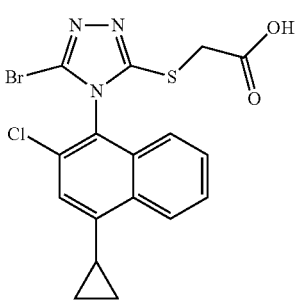
(II)

The present invention provides a levorotary or dextral compound represented by formula (II) or a pharmaceutically acceptable salt thereof, which exists in the form of a single axially chiral isomer or enriched in an axially chiral isomer.

In certain embodiments of the present invention, the levorotary or dextral compound represented by formula (II) or the pharmaceutically acceptable salt thereof has an axially chiral isomer content of ≥60%, preferably ≥70%, more preferably ≥80%, even more preferably ≥90%, most preferably ≥95%.

The present invention also provides a compound represented by formula (III) or a pharmaceutically acceptable salt thereof.

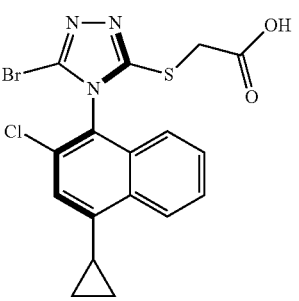
(III)

In certain embodiments of the present invention, the compound represented by formula (III) or the pharmaceutically acceptable salt thereof has an excess content of the axially chiral isomer of ≥90%.

The present invention also provides a compound represented by formula (IV) or a pharmaceutically acceptable salt thereof.

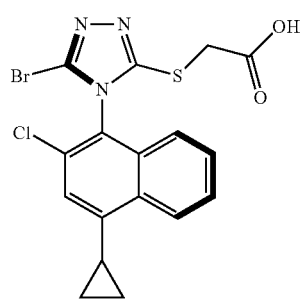
(IV)

In certain embodiments of the present invention, the compound represented by formula (IV) or the pharmaceutically acceptable salt thereof has an excess content of the axially chiral isomer of ≥90%.

In certain embodiments of the present invention, the compound or the pharmaceutically acceptable salt thereof is selected from a compound represented by formula (V).

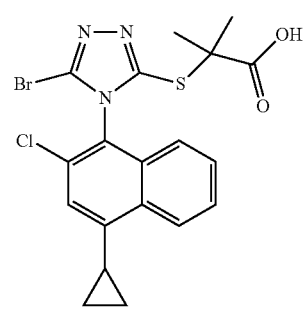
(V)

The present invention also provides a levorotary or dextral compound represented by formula (V) or a pharmaceutically acceptable salt thereof, which exists in the form of single axially chiral isomer or enriched in an axial chiral isomer.

In certain embodiments of the present invention, the levorotary or dextral compound represented by formula (V) or the pharmaceutically acceptable salt thereof has an axially chiral isomer content of ≥60%, preferably ≥70%, more preferably ≥80%, even more preferably ≥90%, most preferably ≥95%.

The present invention also provides a compound represented by formula (VI) or a pharmaceutically acceptable salt thereof.

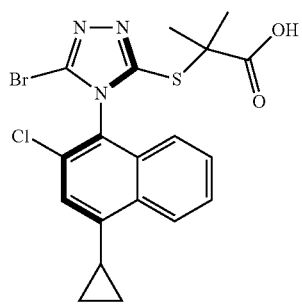

(VI)

In certain embodiments of the present invention, the compound represented by formula (VI) or the pharmaceutically acceptable salt thereof has an excess content of axially chiral isomer of ≥90%.

The present invention also provides a compound represented by formula (VII) or a pharmaceutically acceptable salt thereof.

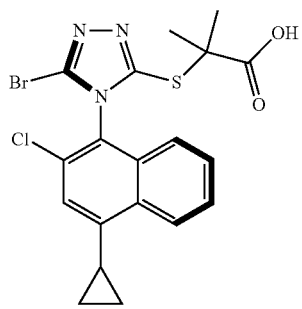

(VII)

In certain embodiments of the present invention, the compound represented by formula (VII) or the pharmaceutically acceptable salt thereof has an excess content of axially chiral isomer of ≥90%.

In certain embodiments of the present invention, Y and Z are linked together, and the moiety

is selected from

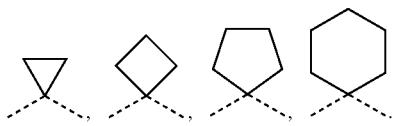

The present invention also provides a pharmaceutical composition which comprises a therapeutically effective amount of the aforesaid compound or the pharmaceutically acceptable salt thereof as an active ingredient, and a pharmaceutically acceptable carrier.

The invention also provides a method of treating disorders closely related to aberrant levels of uric acid comprising administering to a subject a therapeutically effective amount of the aforesaid compound, or the pharmaceutically acceptable salt thereof, or the aforesaid composition.

The present invention also provides a use of the aforesaid compound, or the pharmaceutically acceptable salt thereof, or the aforesaid composition in the manufacture of a medicament for treating disorders closely related to aberrant levels of uric acid.

In certain embodiments of the present invention, the disorders are hyperuricemia, gouty arthritis, kidney stones, urinary calculi or hypertension.

DEFINITIONS OF TERMS

"The levorotary or dextral compound represented by formula (II)" can be a single axially chiral isomer of the compound represented by formula (II) or a mixture enriched in one axially chiral isomer.

"The levorotary or dextral compound represented by formula (V)" can be a single axially chiral isomer of the compound represented by formula (V) or a mixture enriched in one axially chiral isomer.

"Enriched in one axially chiral isomer" refers to the content of one of the axially chiral isomers is <100% and ≥60%, preferably ≥70%, more preferably ≥80%, even more preferably ≥90%, most preferably ≥95%.

"Excess of the axially chiral isomer" refers to the difference between the relative percentages of the two axially chiral isomers. For example, wherein, the content of one of the axially chiral isomer is 90%, and the other one is 10%, then the excess of the axially chiral isomer is 80%.

The compound represented by formula (III) and formula (IV) are the two absolute configurations of the compound represented by formula (II), respectively.

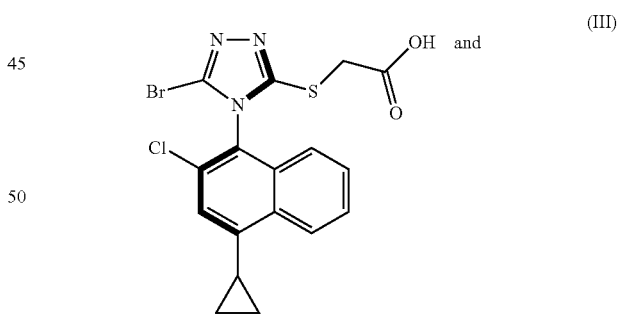

(III)

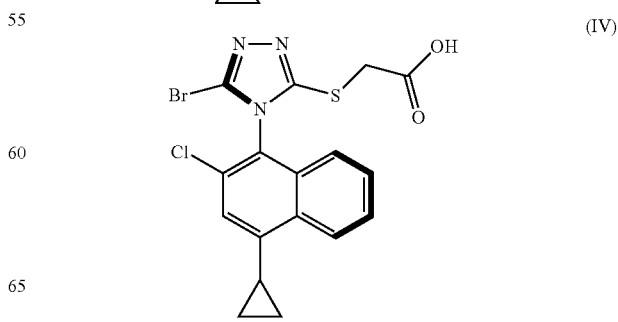

(IV)

are the two absolute configurations of

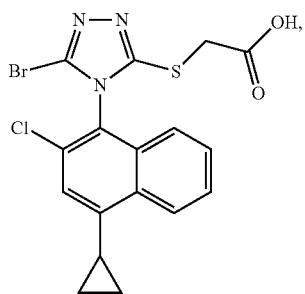

(II)

respectively.

The compound represented by formula (VI) and formula (VII) are the two absolute configurations of the compound represented by formula (V), respectively.

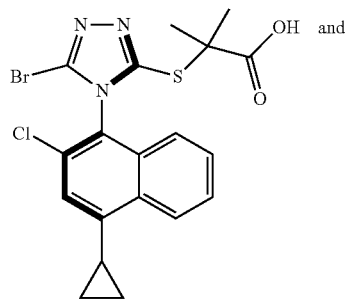

(VI)

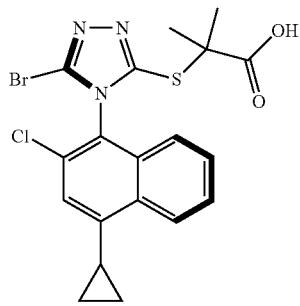

(VII)

are the two absolute configurations of

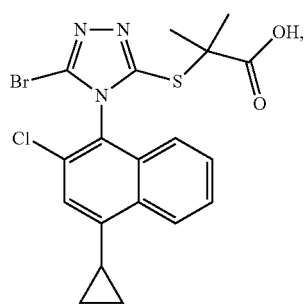

(V)

respectively.

(+) refers to dextrorotation, (−) refers to levorotation, (±) refers to racemization.

The term "pharmaceutically acceptable" used herein is in allusion to those compounds, materials, compositions and/or dosages which are applied to contact to human and animal tissues without excessive toxicity, irritation, anaphylaxis, or other issues or complication, and suit to rational interest and risk ratio within the bounds of reliable medical judgment.

The term "pharmaceutically acceptable salt" refers to salt of the compounds in this invention which are prepared by compounds with certain substituents and relatively nontoxic acids or alkalis. When compounds contain relatively acidic functional group, alkalis-additive salts are prepared by enough alkalis contacting with these compounds in neutral form in pure solutions or appropriate intertia solvents. Pharmaceutically acceptable alkalis-additive salts include sodium, potassium, calcium, ammonium or magnesium salts, or analogous salts. When compounds contain relatively alkaline functional group, acid-additive salts are prepared by enough acids contacting with these compounds in neutral form in pure solutions or appropriate intertia solvents. Examples of pharmaceutically acceptable acid-additive salts include inorganic acid salts, the aforesaid inorganic acids include hydrochloric acid, hydrobromic acid, nitric acid, carbonic acid, bicarbonate radical, phosphoric acid, monohydrogen phosphate, dihydrogen phosphate, sulphuric acid, bisulfate, hydroiodic acid, phosphorous acid and so on; and organic acid, the aforesaid organic acids include acetic acid, propionic acid, isobutyric acid, maleic acid, malonic acid, benzoic acid, succinic acid, octandioic acid, Fumaric acid, lactate, amygdalic acid, alizaric acid, benzenesulfonic acid, p-methylbenzenesulfonic acid, citric acid, tartaric acid, methylsulforic acid and so on; also include amino acid (like arginine) salts, and organic acid salts like glucuronic acid and so on (refer to Berge et al., "pharmaceutical Salts", Journal of pharmaceutical Science 66: 1-19 (1977)). The certain compounds containing alkaline and acidic functional groups in this invention can be transferred into any one of alkaline- or acidic-additive salts.

The neutral form of the compound is preferably regenerated by contacting the salt with alkalis or acids and then isolating the parent compounds in the conventional manner. The parent form of the compound differs from the various salt forms thereof in certain physical properties, such as solubility in polar solvents.

The term "pharmaceutically acceptable salts" used herein is derivatives of compounds in this invention, including, maternal compounds modified through salifying with acids or alkalis. Examples of pharmaceutically acceptable salts include, but are not limited to, alkali bases, such as inorganic acid salts or organic acid salts of amines, acid radicals, such as alkali metal salts or organic salts of carboxylic acids, and so on. Pharmaceutically acceptable salts include normal nontoxic salts or quaternary ammonium salts of maternal compounds, such as nontoxic salts formed from inorganic or organic acids. Normal nontoxic salts include, but are not limited to, those salts derived from inorganic or organic acids, and the aforesaid inorganic or organic acids are selected from 2-acetoxy benzoic acid, 2-hydroxyl ethanesulfonic acid, acetic acid, ascorbic acid, benzenesulfonic acid, benzoic acid, bicarbonate radical, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxyl, hydroxy naphthalene, hydroxyethyl sulfonic acid, lactic acid, lactose, dodecyl sulfonic acid, maleic acid, malic acid, mandelic acid, methanesulfonic acid, nitric acid, oxalic acid, dihydroxy naphthalene acid, pantothenic acid, phenylacetic acid, phosphoric acid, polygalactose aldehyde, propionic acid, salicylic acid, stearic acid, subacetic acid, succinic acid, sulfamic acid, sulfanilic acid, sulfuric acid, tannin, tartaric acid and p-methylbenzenesulfonic acid.

Pharmaceutically acceptable salts in the present invention can be synthesized through conventional chemical methods with maternal compounds containing acid radical or alkaline base. In general, the preparation methods of these salts is that in water or organic solvents or the mixture of both, dissociated acidic or alkaline forms of these compounds react with stoichiometric proper acids or alkalis to give salts. Generally, non-aqueous media like ether, ethyl acetate, ethanol, isopropanol, or acetonitrile or the like are preferred.

The compounds of the present invention may also contain unnatural proportions of atomic isotopes at one or more of the atoms that constitute such compounds. For example, the compounds may be radiolabeled with radioactive isotopes, such as tritium ($^3H$), iodine-125 ($^{125}I$) or carbon-14 ($^{14}C$). All isotopic variations of the compounds of the present invention, regardless of radioactivity or not, are intended to be encompassed within the scope of the present invention.

The term "pharmaceutically acceptable carrier" refers to any formulation or carrier medium that is capable of delivery of an effective amount of an active agent of the present invention, and does not interfere with the biological activity of the active agent, without toxic side effects in a host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005), which is incorporated herein by reference.

The terms "effective amount" or "therapeutically effective amount" for a drug or pharmacologically active agent refers to a nontoxic but sufficient amount of the drug or agent to provide the desired effect. In the oral dosage forms of the present disclosure, an "effective amount" of an active agent of the composition refers to the amount of the active agent required to provide the desired effect when used in combination with the other active agent of the composition. The amount that is "effective" will vary from subject to subject, depending on the age and general condition of a recipient, and also a particular active agent, and an appropriate effective amount in an individual case may be determined by one of ordinary skill in the art using routine experimentation.

The terms "active ingredient" means a chemical entity which can be effective in treating a targeted disorder, disease or symptom.

ADVANTAGE OF INVENTION

A series of compounds reported by the present invention, particularly a rotational isomer of the compound represented by formula (III) ((−)-WX001), the compound represented by formula (IV) ((+)-WX002), the compound represented by formula (VI) ((−)-WX004), the compound represented by formula (VII) ((+)-WX005), compared with the reference racemic compound (±)-Lesinurad, demonstrated significantly improved inhibitory activity in the transport of labeled uric acid in a MDCK cell line stably transfected with the URAT1 gene, wherein the isomer (−)-WX001 demonstrated more than 3-fold inhibitory activity in vitro compared to the other isomer (+)-WX002, fully demonstrating an advantage of the inhibitory activity of a single isomer in vitro. Meanwhile, (−)-WX001 demonstrated lower clearance in vivo and higher plasma exposure in rat PK compared to (+)-WX002 and (±)-Lesinurad at the same dose and in the same administration, and the overall pharmacokinetic performance was better. More strikingly, (−)-WX001 and (+)-WX002, compared with (±)-Lesinurad, showed excellent stability in vitro on hepatocyte metabolic stability test in the same condition in vitro, and no metabolites were detected. We could foresee the single isomer compound containing a substituent on the naphthalene ring, especially the electron-withdrawing group, such as (−)-WX001, (+)-WX002, (−)-WX004 and (+)-WX005 might significantly reduce the likelihood of clinical toxic side effects in clinical administration and maintain or improve clinical efficacy in the body.

DETAILED DESCRIPTION OF THE PREFERRED EMBODIMENT

The present invention will be specifically described below by way of embodiments, but the scope of the present invention is not limited thereto. While the present invention has been described in detail and with reference to specific embodiments thereof, it will be apparent to one skilled in the art that various changes and modifications can be made therein without departing from the spirit and scope thereof.

Embodiment 1 and Embodiment 2: Compound (−)-WX001 (Formula (III)) and (+)-WX002 (Formula (IV))

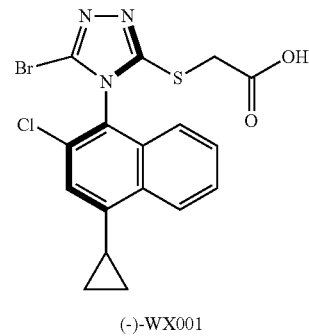

(−)-WX001

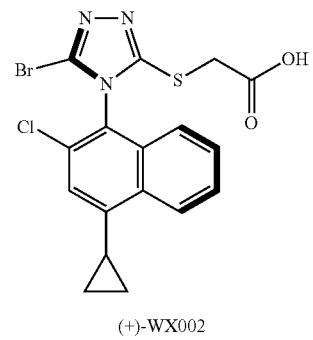

(+)-WX002

Synthesis Route

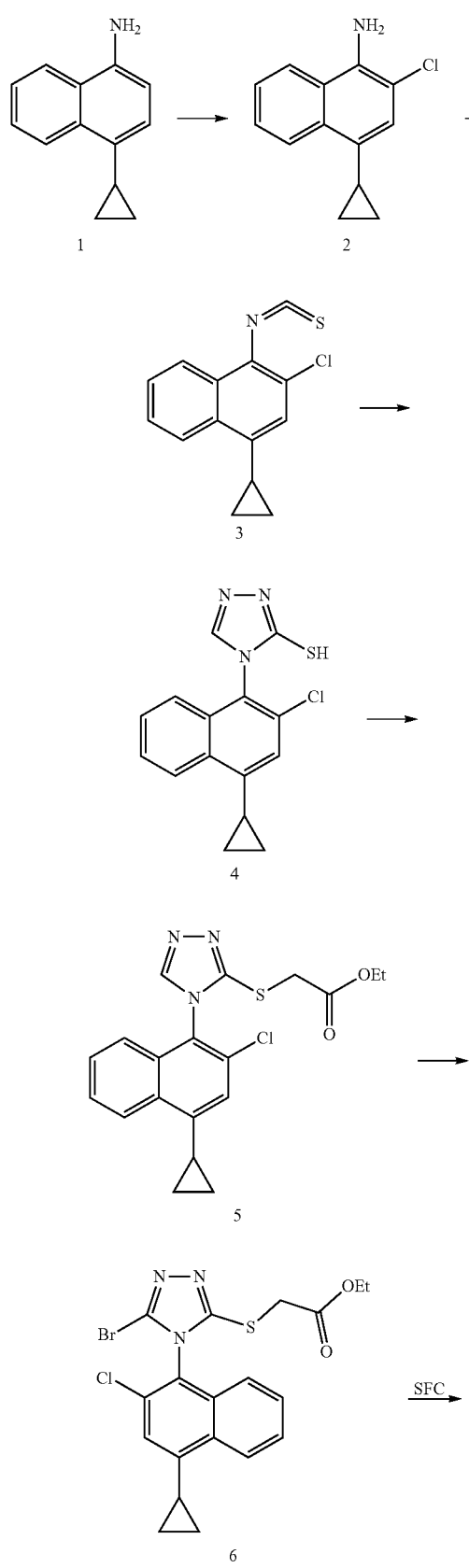

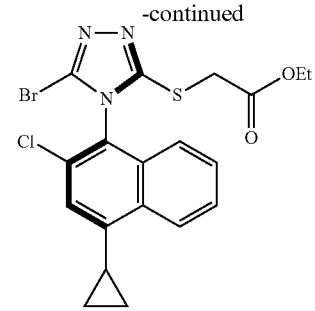

+

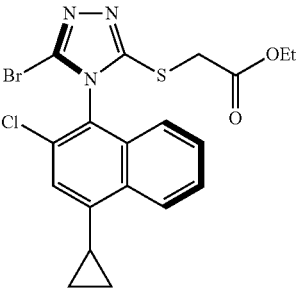

→

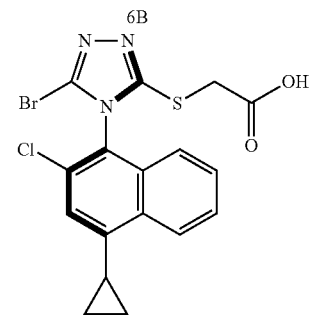

(−)-WX001

+

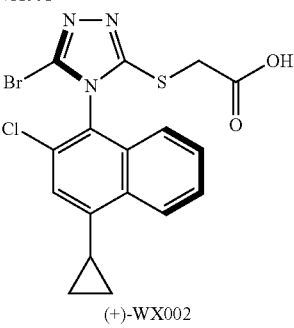

(+)-WX002

Step 1: The Synthesis of Compound 2

The solution of compound 1 (500.00 mg, 2.73 mmol, 1.00 eq) and N-chlorosuccinimide (364.34 mg, 2.73 mmol, 1.00 eq) in acetic acid (5.00 mL) was stirred for 16 h at 20° C. After the reaction finished, the reaction mixture was concentrated to remove acetic acid, and added 1.0 g silica gel to mix sample. The sample was purified by automatic column chromatography (EA/PE=0-10%) to give compound 2 (383.00 mg, 1.76 mmol, 64.47% yield) as brown solid. $^1$H NMR (400 MHz, CDCl$_3$) δ: 8.41-8.35 (m, 1H), 7.85-7.80 (m, 1H), 7.57-7.52 (m, 2H), 7.19 (d, J=0.8 Hz, 1H), 4.43 (s, 2H), 2.26-2.17 (m, 1H), 1.07-0.97 (m, 2H), 0.74-0.67 (m, 2H).

Step 2: The Synthesis of Compound 3

To a solution of compound 2 (360.00 mg, 1.65 mmol, 1.00 eq) and triethylamine (502.02 mg, 4.96 mmol, 687.70 uL, 3.00 eq) in dichloromethane (5.00 mL) was added thiophosgene (228.17 mg, 1.98 mmol, 152.12 uL, 1.20 eq) at 0° C. and the reaction mixture was stirred for 0.5 h at 0° C. The mixture was quenched with dilute hydrochloric acid (1 mol/L, 20 mL) and then extracted with dichloromethane (10 mL×3). The organic phases were combined and washed with sat. NaCl aq. (30 mL), dried over anhydrous $Na_2SO_4$, the drier was filtered out and the filtrate was concentrated to give crude compound 3 (520.00 mg, crude product) as black liquid which was used for the next step.

Step 3: The Synthesis of Compound 4

The solution of crude compound 3 (520.00 mg, 2.00 mmol, 1.00 eq), hydrazine hydrate (100.12 mg, 2.00 mmol, 97.20 uL, 1.00 eq) and N,N-dimethylformamide dimethyl acetal (285.98 mg, 2.40 mmol, 317.76 uL, 1.20 eq) in N,N-dimethylformamide (5.00 mL) was stirred for 16 h at 20° C. The reaction mixture was concentrated to remove N,N-dimethylformamide. The residual mixture was dissolved in ethyl acetate (20 mL) and added silica gel (2 g) to mix sample. The sample was purified by automatic column chromatography (EA/PE=0-35%) to give compound 4 (813.00 mg, crude product) as white solid. $^1$H NMR (400 MHz, Methanol-$d_4$) δ: 8.58 (d, J=8.0 Hz, 1H), 8.37 (s, 1H), 7.73-7.67 (m, 1H), 7.67-7.62 (m, 1H), 7.48-7.45 (m, 1H), 7.38-7.34 (m, 1H), 2.59-2.49 (m, 1H), 1.25-1.18 (m, 2H), 0.96-0.84 (m, 2H).

Step 4: The Synthesis of Compound 5

Added compound 4 (813.00 mg, 2.69 mmol, 1.00 eq), ethyl 2-bromopropionate (539.86 mg, 3.23 mmol, 357.53 uL, 1.20 eq) and cesium carbonate (1.76 g, 5.39 mmol, 2.00 eq) into N,N-dimethylformamide (5.00 mL) and the reaction mixture was stirred for 16 h at 20° C. After the reaction finished, the mixture was concentrated by oil pump to give a mixture of yellow oil and white solid. Acetonitrile (20 mL) was added to the mixture and stirred for 2 min, and the mixture was filtered and the filter cake was washed with acetonitrile (20 mL). The filtrate was combined and concentrated to give crude compound 5 (1.10 g, crude product) as yellowish-brown oil.

$^1$H NMR (400 MHz, $CDCl_3$) δ: 8.49 (d, J=8.4 Hz, 1H), 8.24 (s, 1H), 7.68-7.63 (m, 1H), 7.62-7.59 (m, 1H), 7.39-7.37 (m, 1H), 7.22 (d, J=8.0 Hz, 1H), 4.19-4.17 (m, 2H), 4.16-4.15 (m, 2H), 2.46-2.39 (m, 1H), 1.22-13.18 (m, 2H), 1.06 (t, J=7.2 Hz, 3H), 0.90-0.85 (m, 2H);

MS m/z: 388.0 [M+H]+.

Step 5: The Synthesis of Compound 6

Added compound 5 (1.10 g, crude product), N-bromosuccinimide (505.46 mg, 2.84 mmol, 1.00 eq) into acetonitrile (10.00 mL) and the reaction mixture was stirred for 2 h at 18° C. After the reaction finished, the mixture was concentrated to get mixed sample. The sample was purified by automatic column chromatography (EA/PE=0-25%) to give crude product as brown oil. The crude product was purified by prep-HPLC to give compound 6 (201.1 mg, 430.82 umol) as white solid.

$^1$H NMR (400 MHz, $CD_3OD$) δ: 8.64 (d, J=8.0 Hz, 1H), 7.79-7.74 (m, 1H), 7.74-7.69 (m, 1H), 7.52 (d, J=0.8 Hz, 1H), 7.27-7.22 (m, 1H), 4.17-4.09 (m, 2H), 4.08-3.96 (m, 2H), 2.63-2.52 (m, 1H), 1.28-1.23 (m, 5H), 0.97-0.90 (m, 2H).

MS m/z: 468.0 [M+H+2]$^+$.

Step 6: The Synthesis of Compound 6A & 6B

Compound 6 (201.1 mg, 430.82 umol, 1.00 eq) was separated by supercritical fluid chromatography SFC (chiral column: Chiralpak AD 250 mm×30 mm, 5 um; mobile phase: supercritical $CO_2$/ethanol (0.1% ammonium hydroxide)=30% for 30 min; flow rate: 60 mL/min; wavelength: 220 nm) to give compound 6A (50.30 mg, 107.76 umol) as colorless transparent oil and compound 6B (52.60 mg, 112.69 umol) as colorless transparent oil.

Compound 6A: SFC (chiral column: Chiralpak AD-3 (100 mm×4.6 mm, 3 um); mobile phase: ethanol (0.05% DEA)/supercritical $CO_2$=5-40%, 4.5 min; 40%, 2.5 min; 5%, 1 min; flow rate: 2.8 mL/min; wavelength: 220 nm; column temperature: 40° C.) $R_t$=3.513 min. Excess of the axially chiral isomer: 99.69%.

Compound 6B: SFC (chiral column: Chiralpak AD-3 (100 mm×4.6 mm, 3 um); mobile phase: ethanol (0.05% DEA)/supercritical $CO_2$=5~40%, 4.5 min; 40%, 2.5 min; 5%, 1 min; flow rate: 2.8 mL/min; wavelength: 220 nm; column temperature: 40° C.) $R_t$=3.911 min. Excess of the axially chiral isomer: 99.87%.

Step 7: The Synthesis of Compound (−)-WX001 and (+)-WX002

Added compound 6A (50.00 mg, 107.12 umol, 1.00 eq) and $LiOH·H_2O$ (22.47 mg, 535.60 umol, 5.00 eq) into ethanol (2.00 mL)/$H_2O$ (2.00 mL), and the reaction mixture was stirred for 16 h at 20° C. The mixture was concentrated to remove ethanol, and the pH value of the residual water phase was adjusted to 2 with dilute hydrochloric acid (2 mol/L). The white solid was precipitated and filtered, and the filtrate cake was washed with water (5 mL), dissolved in ethanol (1 mL), added water (20 mL) and lyophilized to give (−)-WX001 (36.30 mg, 82.74 umol, 77.24% yield).

$^1$H NMR (400 MHz, $CD_3OD$) δ: 8.52 (d, J=8.4 Hz, 1H), 7.67-7.55 (m, 2H), 7.39 (s, 1H), 7.13 (d, J=8.0 Hz, 1H), 4.56 (s, 1H), 3.95-3.79 (m, 2H), 2.53-2.39 (m, 1H), 1.18-1.10 (m, 2H), 0.85-0.76 (m, 2H);

MS m/z: 439.9 [M+H+2]$^+$;

SFC (chiral column: Chiralpak AS-3 (150 mm×4.6 mm, 3 um); mobile phase: methanol (0.05% DEA)/supercritical $CO_2$=5~40%, 5 min; 40%, 2.5 min; 5%, 2.5 min; flow rate: 2.5 mL/min; wavelength: 220 nm; column temperature: 35° C.) $R_t$=3.548 min. Excess of the axially chiral isomer: 100%. $[α]^{25}_D$=−0.350 (c=5.0 mg/mL methanol solution).

Added compound 6B (52.00 mg, 111.40 umol, 1.00 eq) and $LiOH·H_2O$ (23.37 mg, 557.00 umol, 5.00 eq) into ethanol (2.00 mL)/$H_2O$ (2.00 mL), and the reaction mixture was stirred for 16 h at 20° C. The mixture was concentrated to remove ethanol, and the pH value of the residual water phase was adjusted to 2 with dilute hydrochloric acid (2 mol/L). The white solid was precipitated and filtered, and the filtrate cake was washed with water (5 mL), dissolved in ethanol (1 mL), added water (20 mL) and lyophilized to give (+)-WX002 (36.80 mg, 83.88 umol, 75.29% yield).

$^1$H NMR (400 MHz, $CD_3OD$) δ: 8.64 (d, J=8.4 Hz, 1H), 7.81-7.67 (m, 2H), 7.51 (s, 1H), 7.26 (d, J=8.0 Hz, 1H), 4.14-3.93 (m, 2H), 2.63-2.53 (m, 1H), 1.30-1.23 (m, 2H), 0.97-0.90 (m, 2H);

MS m/z: 439.9 [M+H+2]$^+$.

SFC (chiral column: Chiralpak AS-3 (150 mm×4.6 mm, 3 um); mobile phase: methanol (0.05% DEA)/supercritical $CO_2$=5~40%, 5 min; 40%, 2.5 min; 5%, 2.5 min; flow rate: 2.5 mL/min; wavelength: 220 nm; column temperature: 35° C.) $R_t$=3.774 min. Excess of the axially chiral isomer: 99.22%. $[α]^{25}_D$=+1.191 (c=4.6 mg/mL methanol solution).

Embodiment 3: Compound (±)-WX003 (Formula (II))

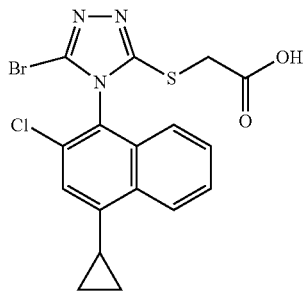 [SMILES: O=C(O)CSc1nnc(Br)n1-c1c(Cl)cc(C2CC2)c2ccccc12]

Synthesis route:

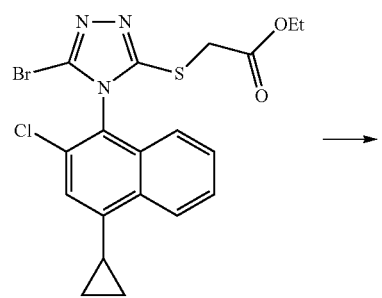

Step 1: The Synthesis of Compound (±)-WX003

Added compound 6 (56.30 mg, 120.61 umol, 1.00 eq) and LiOH.H$_2$O (25.30 mg, 603.07 umol, 5.00 eq) into ethanol (2.00 mL)/H$_2$O (2.00 mL), and the reaction mixture was stirred for 16 h at 20° C. After the reaction finished, the mixture was concentrated to remove ethanol, then added water (2 mL) and the pH value of the residual water phase was adjusted to 3 with dilute hydrochloric acid (2 mol/L). The white solid was precipitated and filtered, and the filtrate cake was washed with water (10 mL), dissolved in ethanol (1 mL), and added water (20 mL) again. The mixture was white without any solid precipitated and lyophilized to give (±)-WX003 (50.30 mg, 114.65 umol, 91.43% yield) as white powder.

$^1$H NMR (400 MHz, CD$_3$OD) δ: 8.64 (d, J=8.4 Hz, 1H), 7.80-7.67 (m, 2H), 7.52 (s, 1H), 7.26 (br d, J=8.4 Hz, 1H), 4.13-3.95 (m, 2H), 2.63-2.53 (m, 1H), 1.30-1.23 (m, 2H), 0.98-0.90 (m, 2H);

MS m/z: 439.6 [M+H]$^+$.

Embodiment 4 and Embodiment 5: Compound (−)-WX004 (Formula (VI)) and (+)-WX005 (Formula (VII))

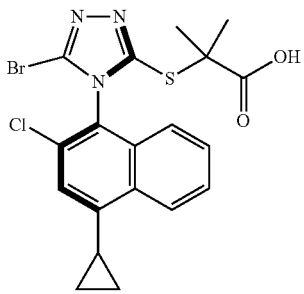

(−)-WX004

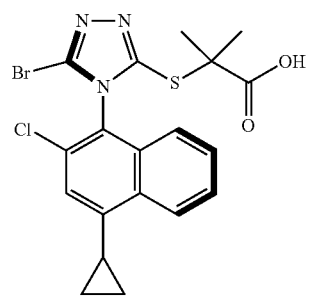

(+)-WX005

Synthesis route:

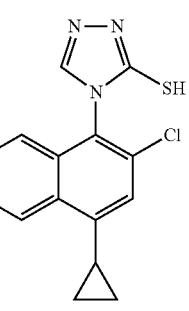

4

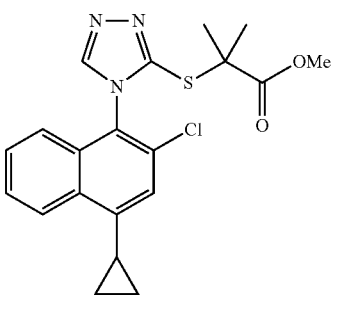

7

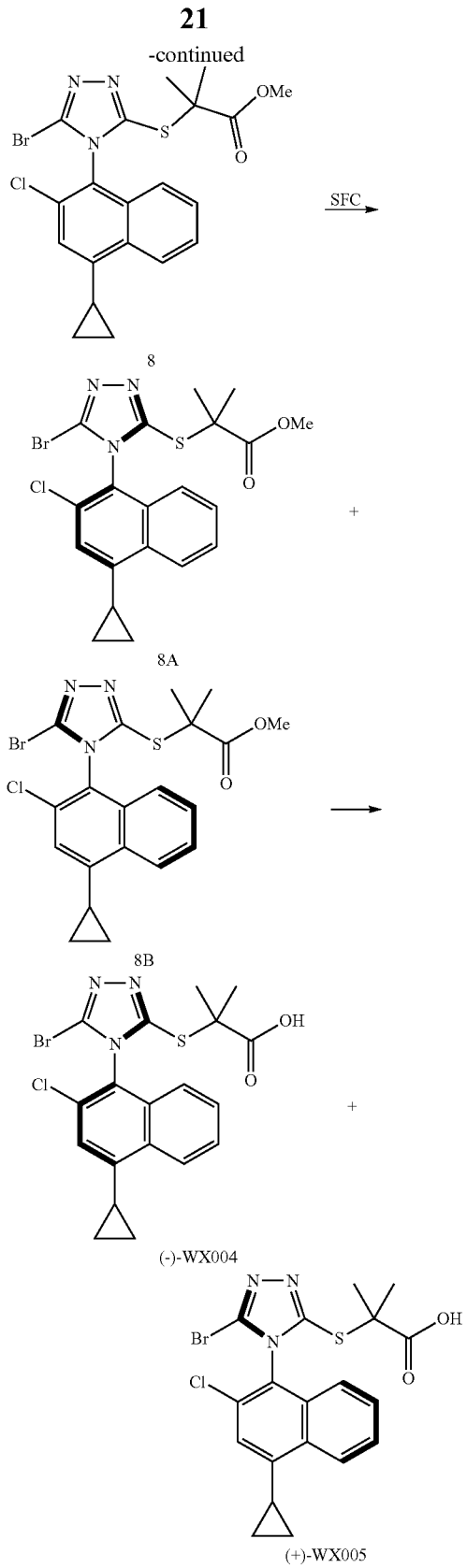

513.61 uL, 1.20 eq) into N,N-dimethylformamide (10.00 mL) and the reaction mixture was stirred for 16 h at 28° C. After the reaction finished, the mixture was concentrated to give a mixture of brown oil. The mixture was soaked with EtOAc (20 mL) and stirred for 10 min. And the mixture was filtered and the filtrate was concentrated to give crude compound 7 (1.52 g, crude product) which was used for next step.

$^1$H NMR (400 MHz, CDCl$_3$) δ: 8.50 (d, J=8.8 Hz, 1H), 8.28 (s, 1H), 7.68-7.63 (m, 1H), 7.62-7.55 (m, 1H), 7.38 (s, 1H), 7.18 (d, J=8.4 Hz, 1H), 3.64 (s, 3H), 2.49-2.38 (m, 1H), 1.68 (s, 3H), 1.61 (s, 3H), 1.24-1.19 (m, 2H), 0.95-0.85 (m, 2H);

MS m/z: 402.1 [M+H]$^+$.

Step 2: The Synthesis of Compound 8

Added crude compound 7 (1.52 g, 1.00 eq), N-bromosuccinimide (1.01 g, 5.67 mmol, 1.50 eq) into acetonitrile (15.00 mL) and the reaction mixture was stirred for 20 h at 28° C. After the reaction finished, silica gel (3.0 g) was added to the mixture, then concentrated to get mixed sample. The sample was purified by fast column chromatography eluted with EA/PE (0~45%) to give compound 9 (0.85 g, 1.77 mmol, 53.44% yield of two steps) as yellow oil.

Step 3: The Synthesis of Compound 8A and 8B

Compound 8 (0.85 g, 1.77 mmol, 1.00 eq) was separated by supercritical fluid chromatography SFC (chiral column: Chiralpak AD 250 mm×30 mm, 5 um; mobile phase: supercritical CO$_2$/methanol (0.1% ammonium hydroxide)=25%; flow rate: 50 mL/min; wavelength: 220 nm) to give compound 8A (350.00 mg, 727.94 umol) as straw yellow oil and compound 8B (350.00 mg, 727.94 umol) as straw yellow oil.

Compound 8A: SFC (chiral column: Chiralpak AD-3 (150 mm×4.6 mm, 3 um); mobile phase: methanol (0.05% DEA)/supercritical CO$_2$=5~40%, 5.5 min; 40%, 3 min; 5%, 1.5 min; flow rate: 2.5 mL/min; wavelength: 220 nm; column temperature: 40° C.) R$_t$=4.972 min. Excess of the axially chiral isomer: 99.72%.

Compound 8B: SFC (chiral column: Chiralpak AD-3 (150 mm×4.6 mm, 3 um); mobile phase: methanol (0.05% DEA)/supercritical CO$_2$=5~40%, 5.5 min; 40%, 3 min; 5%, 1.5 min; flow rate: 2.5 mL/min; wavelength: 220 nm; column temperature: 40° C.) R$_t$=5.242 min. Excess of the axially chiral isomer: 99.05%.

Step 4: The Synthesis of Compound (−)-WX004 and (+)-WX005

Added compound 8A (330.00 mg, 686.34 umol, 1.00 eq) and LiOH.H$_2$O (143.99 mg, 3.43 mmol, 5.00 eq) into methanol (15.00 mL)/H$_2$O (15.00 mL), and the reaction mixture was stirred for 2.5 h at 30° C. After the reaction finished, the mixture was combined with small scale reaction, concentrated at 35° C. to remove methanol, and the pH value of the residual reaction mixture was adjusted to 2 with dilute hydrochloric acid (2 mol/L). Lots of white solids were precipitated and gathered together immediately. The solid was filtered, and the filtrate cake was washed with water (10 mL). The filter cake was dissolved in acetonitrile (1 mL), added water (15 mL) and lyophilized to give (−)-WX004 (328.30 mg, 703.33 umol) as white solid.

$^1$H NMR (400 MHz, MeOD-d$_4$) δ: 8.60 (d, J=8.0 Hz, 1H), 7.76-7.64 (m, 2H), 7.47 (s, 1H), 7.16 (d, J=8.0 Hz, 1H), 2.58-2.50 (m, 1H), 1.63 (d, J=5.2 Hz, 6H), 1.27-1.21 (m, 2H), 0.95-0.88 (m, 2H);

MS m/z: 465.7 [M+H]$^+$, 467.7 [M+H+2]$^+$;

SFC (chiral column: Chiralpak AD-3 (150 mm×4.6 mm, 3 um); mobile phase: ethanol (0.05% DEA)/supercritical CO$_2$=5~40%, 5.5 min; 40%, 3 min; 5%, 1.5 min; flow rate: 2.5 mL/min; wavelength: 220 nm; column temperature: 40°

Step 1: The Synthesis of Compound 7

Added compound 4 (1.00 g, 3.31 mmol, 1.00 eq), potassium carbonate (914.95 mg, 6.62 mmol, 2.00 eq) and methyl 2-bromo-2-methylpropanoate (719.05 mg, 3.97 mmol, C.); $R_f$=4.892 min. Excess of the axially chiral isomer: 97.64%. $[\alpha]^{25}_D$=−5.766 (c=5.52 mg/mL methanol solution).

Added compound 8B (350.00 mg, 727.94 umol, 1.00 eq) and LiOH.H$_2$O (152.72 mg, 3.64 mmol, 5.00 eq) into methanol (16.00 mL)/H$_2$O (16.00 mL), and the reaction mixture was stirred for 2 h at 30° C. The mixture was concentrated at 35° C. to remove methanol, and the pH value of the residual reaction mixture was adjusted to 2 with dilute hydrochloric acid (2 mol/L). Lots of white solids were precipitated and gathered together immediately. The solid was filtered, and the filtrate cake was washed with water (10 mL). The filter cake was dissolved in acetonitrile (1 mL), added water (20 mL) and lyophilized to give (+)-WX005 (324.60 mg, 695.40 umol, 95.53% yield) as white solid.

$^1$H NMR (400 MHz, MeOD-d$_4$) δ: 8.61 (d, J=8.0 Hz, 1H), 7.77-7.63 (m, 2H), 7.48 (s, 1H), 7.17 (d, J=8.0 Hz, 1H), 2.60-2.49 (m, 1H), 1.71-1.54 (m, 6H), 1.27-1.19 (m, 2H), 0.96-0.85 (m, 2H);

MS m/z: 466.0 [M+H]$^+$, 468.0 [M+H+2]$^+$;

SFC (chiral column: Chiralpak AD-3 (150 mm×4.6 mm, 3 um); mobile phase: ethanol (0.05% DEA)/supercritical CO$_2$=5~40%, 5.5 min; 40%, 3 min; 5%, 1.5 min; flow rate: 2.5 mL/min; wavelength: 220 nm; column temperature: 40° C.) $R_f$=5.301 min. Excess of the axially chiral isomer: 91.82%. $[\alpha]^{25}_D$=+7.630 (c=5.38 mg/mL methanol solution).

Testing Embodiment 1: Evaluation In Vitro

1. Experimental Objective

Determination of the IC$_{50}$ value of the inhibitory activity of the compound against uric acid reabsorption by the MDCK cell line stably transfected with the URAT-1 (uric acid transporter) gene.

2. Background Introduction

Gout is a progressive disease induced by abnormal elevation of the uric acid level in blood. The coding URAT-1 gene exists in uric acid transporter in renal tubules. Small molecule compounds can promote uric acid excretion by inhibiting the function of this protein, thereby preventing gout attacks.

3. Experimental Material

URAT-1 (MDCK) cell line: the MDCK cell line stably transfected with the URAT-1 gene
Cell culture medium: MEM culture medium added 10% fetal bovine serum (FBS), 1% sodium pyruvate and 250 ug/ml G418.
HBSS buffer solution.
0.1 M NaOH solution.
Uric acid solution labeled by $^{14}$C.
CO$_2$ incubator.
Liquid scintillation counter Tri-Carb 4. Experimental Procedure and Method 4.1 Cell Inoculation 1) the supernatant of cell culture was aspirated, and cells was washed with 10 mL PBS.
2) preheated trypsin was added into the washed cell culture flask, and which was rotated to make trypsin covering onto the bottom of cell culture flask equably. Cell was dissociated at room temperature.
3) the cells were suspended with 10-15 mL of culture medium in each T150 flask, 0.1 mL was absorbed and diluted with trypan blue solution, and the cells was 2 folds serial counted.
4) cells were diluted to 2.5×10$^5$/mL with the culture medium, and the diluted cells were added into a rat tail collagen-coated 24-well plate (800 uL/well, 2×10$^5$ cells/well). The plate was incubated overnight at 37° C. in a 5% CO$_2$ incubator.

4.2 Cell Preparation 1) cells were seeded into 24-well plate, and supernatant was discarded after 16-18 h. The cells were washed twice using 600 ul HBSS buffer.
2) HBSS buffer was removed and 180 ul of HBSS buffer was added into each well again.

4.3 Preparation, Dilution and Sampling of Compound Solution 1) powder of compounds was dissolved into 100% DMSO, and diluted into 6 concentration points by 3-fold dilution, or into 2 concentration points by 10-fold dilution, and the highest starting concentration was 50 mM.
2) 5 ul DMSO solution in step 1) was transferred into 120 ul of HBSS buffer to make a 25-fold dilution.
3) 10 ul diluted solution in step 2) was added into 24-well plate, and the plate was incubated for 15 min at 37° C. in a 5% CO$_2$ incubator. The final concentration of DMSO was 0.2%. The control well contained 0.2% DMSO without compound.

4.4 Testing $^{14}$C-labelled uric acid was diluted and added into plate, and the final concentration was 50 uM. The plate was incubated for 10 min at 37° C. in a 5% CO$_2$ incubator. After supernatant was discarded, cells were washed with HBSS buffer twice. Cells was lysed with 0.1M NaOH. And then cell lysis solution was collected into liquid scintillation tube and added with liquid scintillation solution. The signal was read by liquid scintillation counter Tri-Carb.

4.5 Data Processing and Analysis

URAT-1 inhibition by the treatment of the compounds was analyzed by calculating the percentage of inhibition according to luminescent data. Non-linear curve fitting analysis on the percent inhibition (inh %) data using GraphPad Prism software generate the IC$_{50}$ value. Experiment results as listed in Table-3.

TABLE 3 testing results of inhibition IC$_{50}$ value of all embodiments against URAT-1

| Embodiment | Compound | IC$_{50}$ |
|---|---|---|
| 1 | (−)-WX001 | 8.0 uM |
| 2 | (+)-WX002 | >20 uM |
| 3 | (±)-WX003 | 10.36 uM |
| 4 | (−)-WX004 | 1.1 uM |
| 5 | (+)-WX005 | 1.4 uM |
| Ref | (±)-Lesinurad | 23.97 uM |

Conclusion: compared with the reference racemic compound (±)-Lesinurad, the compound of the present invention demonstrated improved inhibitory activity against URAT-1.

Testing Embodiment 2: Evaluation In Vitro

1. Experimental Objective

The purpose of this experiment was to confirm the metabolites of a series of compounds after incubation for 120 minutes in human hepatocytes using LC-UV-MS$^n$ (n=1-2) detection. MS and MS$^2$ data were analyzed using Metabo-Lynx™ software after data collection.

2. Experimental Scheme 2.1 Hepatocyte Incubation System

| | |
|---|---|
| Concentration of frozen reserved hepatocyte | $1.0 \times 10^6$ cells/mL |
| Species | human |
| Tested Products | (−)-WX001, (+)-WX002, (±)-Lesinurad |
| Tested Products concentration | 10 μM |
| Incubation medium | William's E culture medium |
| Incubation condition | 37° C., 5% CO2/95% humidity |
| Incubation time | 0, 120 min |
| Incubation volumn | 200 μL |
| Positive control | 7-ethoxycoumarin (7-EC, 30 μM) |

2.2 Sample Processing and Analysis

Alter incubating the sample for 2 h, the protein was precipitated by using acetonitrile containing 01.% formic acid, centrifuged, and the supernatant was taken out and dried an under nitrogen, and dissolved and then injected for analysis.

3. Results of the Experiment 3.1 Identification Results of the Metabolites of Compound (−)-WX001 as Showed in Table-4

TABLE 4

| Metabolite | Retention time (min) | Percentage of ultraviolet area | Metabolic pathways |
|---|---|---|---|
| (−)-WX001 | 9.71 | 100% | NA |

3.2 Identification Results of the Metabolites of Compound (+)-WX002 as Showed in Table-5

TABLE 5

| Metabolite | Retention time (min) | Percentage of ultraviolet area | Metabolic pathways |
|---|---|---|---|
| (+)-WX002 | 9.71 | 100% | NA |

3.3 Identification Results of the Metabolites of Compound (±)-Lesinurad as Showed in Table-6

TABLE 6

| Metabolite | Retention time (min) | Percentage of ultraviolet area | Metabolic pathways |
|---|---|---|---|
| (±)-Lesinurad-M1 | 6.26 | 4.40% | oxidation |
| (±)-Lesinurad | 9.02 | 95.60% | NA |

4. Experimental Conclusion

The experimental data showed that the compound (±)-Lesinurad produced 4.40% of the metabolite M1, while no metabolites were detected in the compounds (−)-WX001 and (+)-WX002 under the same human hepatocyte metabolism. Compared to (±)-Lesinurad, (−)-WX001 and (+)-WX002 demonstrated better stability in hepatocyte in vitro.

Testing Embodiment 3: Evaluation In Vivo

1. Experimental Purpose

Drug concentrations in plasma of (−)-WX001 and (+)-WX002 were measured by LC/MS/MS method at different times after SD rats as tested animals were administered (−)-WX001 and (+)-WX002 by IV (intravenous injection) and PO (gavage), and the pharmacokinetic behavior of the compound in the present invention in rats was investigated, and its pharmacokinetic characteristics were evaluated.

2. Experimental Scheme 2.1 Tested Drugs (−)-WX001 and (+)-WX002

2.2 Tested Animals 12 healthy adult male SD rats were divided into 4 groups (each compound contained IV and PO group), 3 rats per group. SD rats were purchased from Shanghai Slac Laboratory Animal CO.LTD, whose animal production license number was SCXK (Shanghai) 2012-0002.

2.3 Drug Preparation

The appropriate amount of the sample was weighed, added a certain amount of DMSO and ultrasonic dissolved, and then was added 20% hydroxypropyl-β-cyclodextrin solution to give tested compound which was 1 mg/mL 5% DMSO/95% 20% HPCD clear solution used for IV and PO administration.

2.4 Administration

12 SD rats were divided into 4 groups and there were 3 male rats in each group, and administrated by IV, PO, respectively after fasting overnight. The dose of IV was 2 mg/kg and administration volume was 2 mL/kg; the dose of PO was 10 mg/kg and administration volume was 10 mL/kg.

3. Experimental Procedure

In group of IV, about 200 μL of blood was collected at 0.083, 0.25, 0.5, 1, 2, 4, 6, 8, 24 hour after administration, placed in an anticoagulant tube of K2-EDTA, centrifuged at 3000 rpm for 15 minutes, and then plasma was separated and stored at −80° C. In group of PO, blood was collected at 0.25, 0.5, 1, 2, 4, 6, 8, 24 hour after administration, and the other operations were the same as the group of IV. The plasma samples were pretreated through precipitated protein and the plasma concentration was determined by LC/MS/MS method. A linear range of the analytical method was 4.00-6000 nM.

4. Pharmacokinetic Parameters

The experimental results showed that (−)-WX001, (+)-WX002 and (±)-Lesinurad demonstrated different pharmacokinetics in SD-rats. At the same dose, (−)-WX001 demonstrated lower clearance in vivo and higher plasma exposure compared to (+)-WX002 in the same administration, and the total pharmacokinetic was better. Compared to (±)-Lesinurad, (−)-WX001 also demonstrated lower clearance in vivo and higher plasma exposure, and the total pharmacokinetic was also better. Meanwhile, no transformation of two axially chiral isomers was observed in vivo, and a stable single axially chiral isomer remained in the circulation system. Experimental results as showed in Table-7:

TABLE 7

Pharmacokinetic parameters of all embodiments in rats

| | Testing embodiment | | (−)-WX001 | (+)-WX002 | (±)-Lesinurad |
|---|---|---|---|---|---|
| IV (2 mpk) | Starting concentration | $C_0$ (nM) | 11708 | 12891 | 11611 |
| | Half-life | $T_{1/2}$ (h) | 2.86 | 3.51 | 1.80 |
| | apparent volume of distribution | $Vd_{ss}$ (L/Kg) | 0.61 | 0.97 | 0.76 |
| | Clearance rate | Cl (mL/min/Kg) | 2.31 | 4.56 | 5.72 |
| | Area under curve | $AUC_{0\text{-}inf}$ (nM · h) | 32952 | 16775 | 14823 |
| | Detention time | $MRT_{0\text{-}inf}$ (h) | 4.40 | 3.58 | 2.21 |
| PO (10 mpk) | Peak concentration | $C_{max}$ (nM) | 20567 | 11983 | 14496 |
| | Peak time | $T_{max}$ (h) | 1.67 | 1.67 | 2.33 |
| | Half-life | $T_{1/2}$ (h) | 4.86 | 2.68 | 2.46 |
| | Area under curve | $AUC_{0\text{-}inf}$ (nM · h) | 154895 | 77436 | 62491 |
| | Detention time | $MRT_{0\text{-}inf}$ (h) | 7.18 | 4.82 | 4.63 |
| | Bioavailability | F (%) | 94 | 76 | 84 |

What is claimed is:

1. A compound or a pharmaceutically acceptable salt thereof, which is represented by formula (II), 2. The compound or the pharmaceutically acceptable salt thereof according to claim 1, which is selected from a levorotary or dextral compound represented by formula (II) or a pharmaceutically acceptable salt thereof, which exists in the form of a single axially chiral isomer or enriched in an axially chiral isomer,

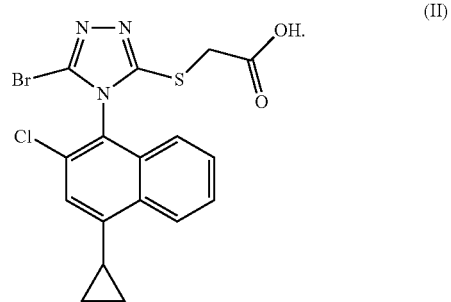 [SMILES: O=C(O)CSc1nnc(Br)n1-c1c(Cl)cc(C2CC2)c2ccccc12]

3. The compound or the pharmaceutically acceptable salt thereof according to claim 2, wherein, an axially chiral isomer content is ≥60%.

4. The compound or the pharmaceutically acceptable salt thereof according to claim 2, wherein the compound is represented by formula (III),

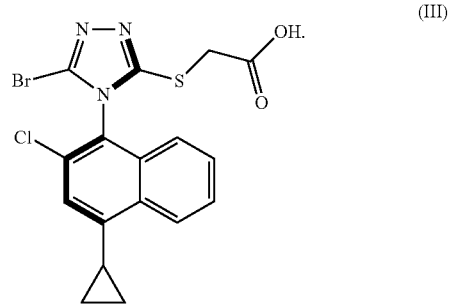

5. The compound or the pharmaceutically acceptable salt thereof according to claim 2, wherein the compound is represented by formula (IV),

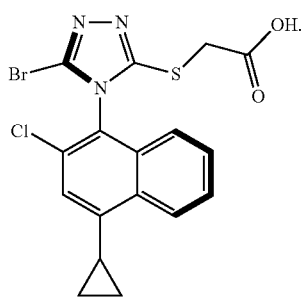

(IV)

6. A pharmaceutical composition comprising a therapeutically effective amount of the compound or the pharmaceutically acceptable salt thereof according to claim 1 as an active ingredient, and a pharmaceutically acceptable carrier.

7. A method of treating disorders closely related to aberrant levels of uric acid, comprising administering to a subject in need thereof a therapeutically effective amount of the compound, or the pharmaceutically acceptable salt thereof according to claim 1.

8. A pharmaceutical composition comprising a therapeutically effective amount of the compound or the pharmaceutically acceptable salt thereof according to claim 4 as an active ingredient, and a pharmaceutically acceptable carrier.

9. A pharmaceutical composition comprising a therapeutically effective amount of the compound or the pharmaceutically acceptable salt thereof according to claim 5 as an active ingredient, and a pharmaceutically acceptable carrier.

10. A method of treating disorders closely related to aberrant levels of uric acid, comprising administering to a subject in need thereof a therapeutically effective amount of the composition according to claim 6.

11. A pharmaceutical composition comprising a therapeutically effective amount of the compound or the pharmaceutically acceptable salt thereof according to claim 2 as an active ingredient, and a pharmaceutically acceptable carrier.

12. A pharmaceutical composition comprising a therapeutically effective amount of the compound or the pharmaceutically acceptable salt thereof according to claim 3 as an active ingredient, and a pharmaceutically acceptable carrier.

13. A method of treating disorders closely related to aberrant levels of uric acid, comprising administering to a subject in need thereof a therapeutically effective amount of the compound, or the pharmaceutically acceptable salt thereof according to claim 2.

14. A method of treating disorders closely related to aberrant levels of uric acid, comprising administering to a subject in need thereof a therapeutically effective amount of the compound, or the pharmaceutically acceptable salt thereof according to claim 3.

15. A method of treating disorders closely related to aberrant levels of uric acid, comprising administering to a subject in need thereof a therapeutically effective amount of the compound, or the pharmaceutically acceptable salt thereof according to claim 4.

16. A method of treating disorders closely related to aberrant levels of uric acid, comprising administering to a subject in need thereof a therapeutically effective amount of the compound, or the pharmaceutically acceptable salt thereof according to claim 5.

17. The compound or the pharmaceutically acceptable salt thereof according to claim 2, wherein, an axially chiral isomer content is ≥70%.

18. The compound or the pharmaceutically acceptable salt thereof according to claim 2, wherein, an axially chiral isomer content is ≥80%.

19. The compound or the pharmaceutically acceptable salt thereof according to claim 2, wherein, an axially chiral isomer content is ≥90%.

20. The compound or the pharmaceutically acceptable salt thereof according to claim 2, wherein, an axially chiral isomer content is ≥95%.

* * * * *